US009692989B2

(12) United States Patent
Jones

(10) Patent No.: US 9,692,989 B2
(45) Date of Patent: Jun. 27, 2017

(54) METHOD OF VALIDATING A CLEANING PROCESS

(76) Inventor: Ian Jones, Co. Wicklow (IE)

( * ) Notice: Subject to any disclaimer, the term of this patent is extended or adjusted under 35 U.S.C. 154(b) by 717 days.

(21) Appl. No.: 13/885,497

(22) PCT Filed: Nov. 14, 2011

(86) PCT No.: PCT/EP2011/070060
§ 371 (c)(1),
(2), (4) Date: May 15, 2013

(87) PCT Pub. No.: WO2012/065952
PCT Pub. Date: May 24, 2012

(65) Prior Publication Data
US 2013/0229516 A1    Sep. 5, 2013

(30) Foreign Application Priority Data

Nov. 18, 2010  (IE) .................................. S2010/0730

(51) Int. Cl.
| H04N 5/33 | (2006.01) |
| G01N 21/35 | (2014.01) |
| G01N 21/359 | (2014.01) |
| G01N 21/94 | (2006.01) |
| G01N 21/3563 | (2014.01) |
| G01N 21/3577 | (2014.01) |

(52) U.S. Cl.
CPC .............. *H04N 5/33* (2013.01); *G01N 21/35* (2013.01); *G01N 21/359* (2013.01); *G01N 21/3563* (2013.01); *G01N 21/94* (2013.01); *G01N 21/3577* (2013.01)

(58) Field of Classification Search
CPC ........ A61N 5/0613; H04N 5/33; G06F 19/20; G01N 21/35
See application file for complete search history.

(56) References Cited

U.S. PATENT DOCUMENTS

| 7,557,923 B2 | 7/2009 | Lodder | |
| 2005/0151965 A1* | 7/2005 | Bissett | G01J 3/28 356/328 |
| 2006/0282223 A1* | 12/2006 | Lewis | A61K 31/00 702/19 |
| 2008/0315134 A1* | 12/2008 | Ehm | G03F 7/7085 250/504 R |

FOREIGN PATENT DOCUMENTS

DK              EP 1677099 A1 *  7/2006  ............. G01N 21/47

* cited by examiner

*Primary Examiner* — David Porta
*Assistant Examiner* — Faye Boosalis
(74) *Attorney, Agent, or Firm* — Schmeiser, Olsen & Watts LLP

(57) ABSTRACT

A method of validating or verifying a process for cleaning a surface contaminated with at least one chemical substrate, comprising the steps of: capturing an infrared image of the surface using infrared chemical imaging; utilizing at least one algorithm to interpret the captured image to extract an infra-red signal from the at least one chemical substrate to determine the amount of the at least one chemical substrate present on the surface; and determining if the amount of the at least one detected chemical substrate exceeds a threshold value, thereby indicating that a repeat cleaning process is required or thereby indicating that no further cleaning is required.

14 Claims, 19 Drawing Sheets

Figure 13

```
Pre-processing of hypercube function Data=preprosshypercube3(filename,crop,units,wgroup,shape,sm)
%     Data=preprosshypercube3(filename,crop,units,wgroup,shape,sm);
%     filename = name of the file to be read it
%     crop = 1 crops hypercube, 0 don't crop image
%     units = 0 convert reflectance to log(1/R)
%             1 converts reflectance to Kubelka-Munk units
%             2 keep reflectance units (default)
%     wgroup = 1 selects regions of interest (ROI), 0 does not select ROI
%     shape = 1 the shape of the ROI is rectangular, 0 the shape of ROI is
%             ellipsoid
%     sm =    1 smooths with Savitzky-Golay filter 9 points, second order
%             polynomial (default), 0 does not smooth.

% imagel is the hypercube, p are the dimension of hypercube
[imagel,p,wavelength]=enviread_aoife(filename);
wavelength=880:7:1720; %% Vis-NIR version Spectral scanner doesn't provide
the rigth information
%% trim spectra
imagel=imagel(:,:,11:113); % Noisy part of the spectra is removed
wavelength=wavelength(11:113);
% imagel(imagel<eps)=eps; % Replace 0 values for eps (2.2204e-016)
% imagel(imagel>1.2)=1.2; % Replace large reflectance to 1.2

%% Defining region of interest
if (nargin>1)&& crop
    [select,limits]=roi_image(imagel,'rectangle');
    imagel=imagel(limits(1):limits(2),limits(3):limits(4),:);
end
p=size(imagel);
npxl=p(1)*p(2);

%% Convertion of reflectance to log(1/R) or K-M units
if exist('units','var')~=1
    units=2;
end
switch units
    case 0
        unit='Log(1/R)';
        imagel(imagel<eps)=eps; % Replace 0 values for eps (2.2204e-016)
        imagel=log10(1./imagel);
        imagel(imagel>2.5)=2.5; % Replace large reflectance to 2.5
    case 1
        unit='KM';
        imagel(imagel<eps)=eps; % Replace 0 values for eps (2.2204e-016)
        imagel=((1-imagel).^2)./(2*imagel);
    case 2
        unit='R';
end
```

Figure 13... cont

```
%% Smoothing with Savitzky Golay and eliminating noisy wavelength
if (nargin<6)|| (sm==1)
    image1=savgol(reshape(image1,npx1,p(3)),9,2,0);
    image1=reshape(image1,p);
    smooth='Savitzky-Golay 9 points, second order polynomial';
% elseif (sm==2)
%     image1=denoisepca(image1);
%     smooth='10 first principal components';
else
    smooth='No';
end %% Create a mask to remove background, group(:,1)
h1=figurescrsz;
switch units
    case 0
        mimage1=min(image1,[],3);
        upxlim=2.5;
        threshold=0.9;
        h2=selthreshold(h1,mimage1,npx1,upxlim);
        mask=mimage1<threshold;
    case 2
        mimage1=max(image1,[],3);
        upxlim=1.2;
        threshold=0.12;
        h2=selthreshold(h1,mimage1,npx1,upxlim);
        mask=mimage1>threshold;
    otherwise
end
imshow(mask,'Parent',h2(3))
...
group(:,1)=reshape(mask,npx1,1);
clear minimage1 accepted
close(h1)
image1=reshape(image1,npx1,p(3));

%% selecting groups if (nargin>3) && wgroup
    SE=strel('disk',5);
    mask=reshape(imerode(reshape(group(:,1),p(1:2)),SE),npx1,1);
    h=figurescrsz;
    imshow(falsergb2(reshape(image1,p),0,mask),[]);
    M=input('Number of groups?');
    close(h)
    if M>0
        group=[group,false(npx1,M)];
        if shape
group(:,2:end)=roi_image(reshape(SNV(image1),p),'rectangle',M,0,mask);
        else
group(:,2:end)=roi_image(reshape(SNV(image1),p),'ellipse',M,0,mask);
        end
    end
end
```

Figure 13... cont

```
%% Save data
data=struct('Path',pwd,'File_name',filename,'Units',unit,'Smooth',smooth,...
    'Threshold',threshold);
Data=struct('X',imagel,'p',p,'group',group,'npxl',npxl,'wavelength',...
    wavelength,'data',data);
save(filename,'Data')
end

...

function mask=mmask(units,threshold,mimagel)
switch units
    case 0
        mask=mimagel<=threshold;
    case 2
        mask=mimagel>=threshold;
end
end
```

Figure 14

PLS-DA Partial least squares discriminant analysis

```
function [B,T,P,W,c,Xmean,ymean] = plsme3(X,y,g,centre)
%    [B,T,P,W,c,Xmean,ymean] = plsme3(X,y,g,centre);
%    to calculate X & y average

[M k]=size(X);
Xmean=mean(X);
ymean=mean(y);

% to centre data
if nargin==4 && centre
    XcN=X-(ones(M,1)*Xmean);
    ycN=y-ymean;
    Xpls=XcN;
    ypls=ycN;
else
    Xpls=X;
    ypls=y;
end
% initilising variables
W=zeros(k,g);
P=zeros(k,g);
c=zeros(g,1);
T=zeros(M,g);
B=zeros(k,g);
% loop
warning off
for j=1:g
    W(:,j)=Xpls'*ypls/norm(Xpls'*ypls);
    T(:,j)=Xpls*W(:,j);
    if j > 1
        T(:,j) = T(:,j) - T(:,1:j-1) * (inv(T(:,1:j-1)'*T(:,1:j-1)) *...
            (T(:,j)' * T(:,1:j-1))');
    end
    c(j,1)=T(:,j)'*ypls/(T(:,j)'*T(:,j));
    P(:,j)=Xpls'*T(:,j)/(T(:,j)'*T(:,j));
    Xpls=Xpls-T(:,j)*P(:,j)';
    ypls=ypls-T(:,j)*c(j);
    B(:,j)=W(:,1:j)*(P(:,1:j)'*W(:,1:j))^-1*c(1:j);
end
```

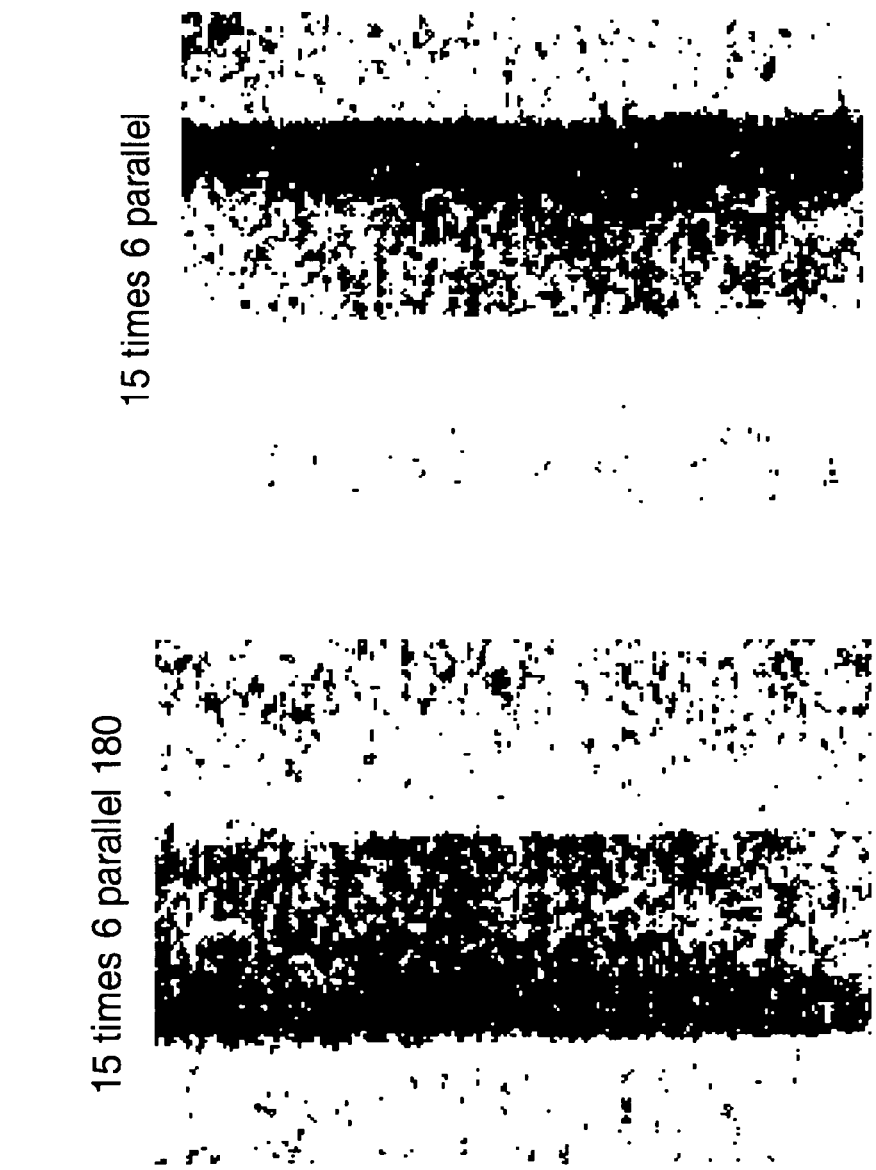
Figure 16....cont

METHOD OF VALIDATING A CLEANING PROCESS

FIELD OF THE INVENTION

The present invention relates to the spectroscopic evaluation of a substance or product on a surface. In particular, the present invention relates to use of such evaluation in a method of validation or verification of a cleaning process of a surface. The surface may be that of pharmaceutical manufacturing equipment and the method comprises spectroscopic evaluation of a substance or product on a surface.

BACKGROUND TO THE INVENTION

In many manufacturing processes, and in particular, in the pharmaceutical manufacturing industry, the removal of potentially harmful contaminants from all product contact equipment is of vital importance. It ensures the safety, efficacy and quality of all products that are manufactured using the equipment.

The cleaning procedure utilised in such industries must be validated to verify its effectiveness, based on pre-determined acceptance criteria. Cleaning process validation is thus executed on all product manufacture contact equipment to ensure and verify the removal of all harmful and unwanted contaminants, such as active ingredients, detergents, and microbes, from the equipment prior to its use in another procedure. Cleaning process validation is of the utmost importance, for example, in situations where pharmaceutical process equipment is used for the manufacture of multiple products in succession, for example, as found on a batch manufacture schedule. In this instance, cleaning process validation ensures that there is no cross contamination between individual batches, different products etc., and thus serves to eliminate the risk of the manufacture of contaminated drug products which is wasteful and expensive.

Currently, in the pharmaceutical industry an equipment cleaning process is typically validated by a user swabbing a product contact surface of the equipment after the cleaning process has been completed. The swabs are subsequently analysed by the user, predominantly using HPLC analysis. Significant manufacturing downtime may result, as the manual swabbing procedure and subsequent analytical activity testing may take up to three days to generate approved results, and the equipment cannot be used until approved results are available. As a result, there are several drawbacks and challenges associated with such a cleaning validation process. Trained personnel are required to develop a cleaning validation protocol, as well as to conduct the manual swabbing and the subsequent laboratory analysis. Manual swabbing introduces the risk of human error by way of incomplete or inaccurate sampling of the cleaned surface. The time taken to generate approved results can also have a serious impact on cycle time for the pharmaceutical equipment. There is also the regulatory burden on the user of conducting and maintaining cleaning validation activities on all product contact equipment on site.

There are currently three phases to cleaning procedure implementation, namely, development, validation, and on-going assessment. Cleaning procedure development studies determine cleaning feasibility and investigate whether the cleaning procedure will adequately remove process soils from product-contact equipment surfaces associated with the blending processes. The understanding of soils and the development of cleaning chemistries are fundamental in delivering successful and appropriate cleaning process. The chemistry or agent employed to clean soiled equipment surfaces should be based on the soil characteristics and in-use process parameters. Following development of a cleaning procedure, validation and controls assure that the developed and validated procedure employed is instituted.

As previously stated, cleaning validation is performed to ensure that production materials that come into contact with the blending equipment surfaces, including utensils, are not contaminated or adulterated. A cleaning validation study typically requires a minimum of three consecutive, successful verification runs. In the absence of three batches or other unique circumstances, cleaning verification is performed to ensure the equipment is suitable prior to the next use, however validation using at least 3 consecutive, successful verification runs is eventually necessary. Cleaning validation for cross-contamination relies upon validated analytical methods for the API or selected marker(s). Generally, the core elements of a cleaning validation protocol contains:

A full description of the cleaning process;
The quantities of each material needed;
The exact pieces of equipment and utilities which can be used, confirmation of their respective qualification and calibration statuses;
The recipe (including defined Critical Process Parameters, CPP's);
The sampling plan including directions for swabbing or rinse collection acceptance criteria and justification of same;
Methods of analysis of test results;
References to applicable procedures, policies and guidelines both internal to the organisation and regulatory bodies including what procedure to follow in the event of an out of specification result or a deviation from the protocol;
Roles and responsibilities of all parties involved;
Approval by the Quality Unit.

The validation process also addresses possible variations in microbiological flora, using a risk-based assessment considering route of administration (i.e. oral, parenteral, topical) and nature of the product. The use profile of the equipment is determined, documented, and categorized into dedicated product/product family equipment or multi-product equipment. Equipment hold times are also considered during a cleaning validation study. Equipment is cleaned as soon as practical after use. Maximum holding times are set between use and cleaning, and cleaning and sampling. The cleaning validation incorporates three runs at the maximum holding time.

The following approaches are typically adopted for multi-product equipment used for manufacturing dosage forms unless special toxicological concerns have been established. The 1/1000 approach may not be suitable for API manufacture, so the 10 ppm approach, or visual determination if that is more conservative, can be substituted.

The 1/1000 Approach:
Not more than 1/1000 of the total minimum daily dose for a 70-kg adult will appear in the maximum daily dose of the next product, except for equipment utilized for paediatric dosage for which a weight adjustment needs to be made accordingly. Refer to the appropriate regulatory guidance for paediatric dosage.

The 10 ppm Approach (Except for Highly Potent Product):
Not more than 10 ppm of the product being cleaned will appear in the next product.

Visual determination with criteria should also be performed in addition to quantitative methods of analysis.

Highly potent product (special toxicological consideration). The approach shall be individually considered and limits set and justified. Dedicated equipment may be necessary.

For cleaning agent residue, limits no more than 1/10,000 of the $LD_{50}$ value for a 70-kg adult appear in the maximum daily dose of the next product for all cleaning agents except for equipment utilized for paediatric dosage for which a weight adjustment needs to be made accordingly. If cleaning development studies demonstrate that water alone is capable of satisfactorily cleaning blending equipment, not only is the cleaning process simplified, but also the validation.

Visual inspection of equipment is performed to align the validation of the cleaning process with the routine inspection of equipment after cleaning. For some products, a visual determination of cleanliness shall be justified when calculations of acceptance criteria for the residual marker(s) is higher than a visual residue determination. This is frequently used for less toxic compounds and especially where an opacifier, such as titanium dioxide, is part of the blend.

At the completion of a validation study, the following activities are in place:
  Review of SOPs to assure that they conform to the validated parameters, and inclusion in the equipment status control system.
  Recording of routine cleaning operations;
  Implementation of change control for the validated equipment and product;
  Inclusion in the Validation Master Plan;
  Controls over cleaning utensils;
  Control over cleaning agents including release by the Quality Unit;
  An ongoing monitoring program of the effectiveness of the cleaning program shall be considered, including periodic verification studies. Special consideration shall be given to highly potent products and microbial cleanliness after storage. Alternately, a means of continuous monitoring, such as PAT, may be employed. Frequently, the final rinsate is tested for conductivity/resistance to determine if the blending equipment cleaning was satisfactory. The level and sensitivity of the testing of final rinsate may depend upon the quality of the water used for that final rinse.

The above outlined current approach to cleaning procedure development and validation is a time consuming and costly process that significantly inhibits clinical trial manufacture activities (because of once-off swabbing requirements following each mini-batch manufactured) and ongoing commercial manufacturing activities (because of the burden associated with cleaning procedure validation).

The use of visual inspection as an assessment criterion for equipment cleaning effectiveness has always been a component of cleaning programs. Mendenhall proposed the use of only visual examination to assess equipment cleanliness in 1989[3]. He summarised that visible cleanliness criteria were more rigid than quantitative calculations and therefore adequate. The US food and Drug Administration acknowledges the use of visually clean criteria for product dedicated equipment. LeBlanc has also reviewed the use of visual examination as the sole acceptance criteria for cleaning validation[4].

A Visible-residue Limit (VRL) is the quantity of marker (usually API) remaining on manufacturing equipment surfaces when it has reached a visually detectable level. An Acceptable-residue Level (ARL) is the amount of marker (usually API) that can remain on manufacturing equipment surfaces and carry over to the next formulation with no pharmacological or adulteration risk. Forsyth et al[5] propose that VRL's could be adopted as the primary acceptance criteria during cleaning evaluation activities if the VRL is calculated to be less than the ARL. They cited the following advantages of a properly validated and maintained VRL program:
  VRL involves testing all visible equipment surfaces—not just swabbed areas during routine validation activities;
  VRL inspections reduce the personnel time needed to swab the manufacturing equipment;
  They eliminate ongoing analytical resources beyond the initial validation;
  Method development and validation resources for new development compounds are not required;
  With the expanded use of VRL data in lieu of surface testing, the extent of testing and documentation necessary for each assessment is reduced, as well as the cost for long-term storage of the documentation and data;
  The manufacturing team have instant availability of visual-testing results, which minimises equipment down-time while waiting for analytical results, therefore increasing manufacturing productivity.

Forsyth et al identified the following risks and limitations when using VRL's
  The potential that dirty equipment passes visual inspection and the subsequent manufactured formulation is adulterated. It was acknowledged that the closer the VRL is to the ARL, the greater the risk becomes;
  To date, VRL determinations have been limited to stainless steel surfaces. The consistency of VRL assessments from transparent equipment materials may be considerably more challenging;
  VRL approaches also have limitations with respect to assessing microbiological control;
  The subjectivity of observers and the variability of interpretation of 'visually clean' is also identified as a risk of using ARL's[6];
  The impact of environmental factors (especially light levels) may also impact the individual interpretation of 'visually clean' criteria. This is particularly a challenge with large scale manufacturing equipment;
  The limitation of such an approach to low potency API's where the ARL's are sufficiently high to be greater than the VRL's.

Within the FDA draft guidance document on Process Validation, it is defined as the collection and evaluation of data, from the process design stage throughout production, which establishes scientific evidence that a process is capable of consistently delivering quality products. Process validation involves a series of activities taking place over the lifecycle of the product and process. This guidance describes the process validation activities in three stages.

Stage 1—Process Design: The commercial process is defined during this stage based on knowledge gained through development and scale-up activities.

Stage 2—Process Qualification: During this stage, the process design is confirmed as being capable of reproducible commercial manufacturing.

Stage 3—Continued Process Verification: Ongoing assurance is gained during routine production activities that the process remains in a state of control.

However there vulnerabilities associated with such an approach, in particular the person-to-person variability of 'visually clean' equipment and the lighting challenges associated with commercial scale equipment. Even with considerable training and experience these risks may remain.

Some examples of alternative technologies currently used to continuously verify equipment cleaning process are as follows:

Lab Based Technologies:
Ion Mobility Spectrometry

Ion mobility spectrometry is a type of separation technique, similar to time of flight mass spectrometry, that distinguishes ions of a given compound based on their velocities through a drift tube under the influence of a weak electric field. It is a fast and specific off-line tool for verifying the cleanliness of pharmaceutical equipment. Recovery percentages and standard deviations for IMS samples are consistent with those obtained with HPLC analysis, but sample throughput of IMS is about 50 times faster[7]. The disadvantages associated with such a method are that it is an off-line analytical tool that requires sample swabbing and preparation activities.

LC-MS-MS

For low-dose compounds, equipment requiring low residue limits, and compounds lacking strong chromophores, the enhanced sensitivity and selectivity of liquid chromatography-mass spectrometry-mass spectrometry (LC-MS-MS) facilitates rapid method development for the detection of low levels of residues of active pharmaceutical ingredients[8]. Like Ion Mobility Spectrometry, the disadvantages associated with LC-MS-MS are that it is an off-line analytical tool that requires sample swabbing and preparation activities.

At-Line Technologies:
ATP Luminescence

ATP luminescence-based technologies may be used to evaluate the level of microbial contamination following the completion of an equipment cleaning process. This is a rapid method of swab analysis that is an accepted method within the food and beverage industries.

On-line Technologies:
UV-Vis Spectrophotometry

UV-Vis technologies monitor rinse effluent to quantify the level of API remaining. When the level of API in the rinse effluent reaches an acceptable level the cleaning process end-point is reached. This is a novel approach that has significant benefits for identification of cleaning process endpoint. One disadvantage identified may be associated with the non-detection of API if it is adhered to the vessel wall following prolonged dirty hold-time studies.

TOC

TOC is a technology that may have potential for monitoring of rinse effluent following an equipment cleaning process in particular for detergents. It has excellent sensitivity capability however the method is non-specific and is also limited as the potential contamination remaining on the equipment surface, if remaining, will not be detected.

Single Point NIR

Portable single point Mid IR systems have been developed for real-time, in-situ surface analysis using grazing-angle infrared spectroscopy. Organic films and coatings on metal and glass surfaces can be measured and identified in seconds[9]. The system was originally developed for use in the aerospace industry. Single point NIR technology does not however generate an image of the sample area or provide a calculation of the concentration of target residue remaining on the surface.

U.S. Pat. No. 7,557,923 relates to multipoint analysis of the presence or concentration of an analyte on a surface using a single point NW system. Point-source spectroscopic assessments do not provide information on spatial distribution of different constituents. In other words, NIR and Raman spectroscopy can only provide information on a very narrow sample site and so do not lend themselves to quantifying over a given area at a single point in time.

Chemical Imaging (CI) is an emerging platform technology that integrates conventional imaging and spectroscopy to attain both spatial and spectral information from an object. Near infrared-chemical imaging (NIR-CI) is the fusion of near-infrared spectroscopy and image analysis. NIR Chemical Imaging has been used for purposes within pharmaceutical manufacturing for the assessment of homogeneity of blended materials and tablets. It can be used to visualize the spatial distribution of the chemical compounds in a sample, providing a chemical image. Each sample measurement generates a hyperspectral data cube containing thousands of spectra. An important part of a NIR-CI analysis is the data processing of the hyperspectral data cube.

By combining the chemical selectivity of vibrational spectroscopy with the power of image visualisation, Chemical Imaging enables a more complete description of the sample. The large number of individual spectra acquired across the spatial dimension of heterogeneous compounds provides a basis from which relative concentrations can be determined for each spatial location. Alternatively, these individual concentrations may be added together to give the total concentration of a specific material within the sample area.

Chemical Images are made up of hundreds of contiguous wavebands for each spatial position of a target studied. Consequently, each pixel in Chemical Image contains the spectrum of that specific position. The resulting spectrum acts like a fingerprint, which can be used to characterise the composition of that particular pixel. There are two basic methods to construct the chemical image. On method involves acquisition of simultaneous spectral positions. The object is moved underneath an imaging spectrograph—this is termed pushbroom acquisition. The other method involves keeping the image field of view fixed and obtaining images one wavelength after another—this is termed staring imager configuration[11].

OBJECT OF THE INVENTION

It is an object of the current invention to provide a method of verification or validation of a cleaning process of any surface. The method comprises the use of Near Infrared-Chemical Imaging (NIR-CI) or Mid-Infrared Chemical Imaging (MIR-CI) to provide spectroscopic information on a sample site or surface and to identify and/or quantify the level of contaminant on the sample site or surface, following a cleaning process.

It is a particular object of the invention to provide a method of verification or validation of a cleaning process carried out on a machine, a piece of equipment, a tool or any utensil used in the manufacture of health products, medicines or pharmaceuticals or any laboratory equipment or machinery or any work surface.

It is a further object of the invention to provide a rapid method of verification or validation of a cleaning process. It is a still further object of the invention to provide a method of assessing homogeneity of blended materials or a tablet.

Another object of the invention is to provide a method of detection of counterfeit pharmaceutical tablets.

SUMMARY OF THE INVENTION

A first aspect of the invention provides a method of verification or validation of a cleaning process, the cleaning process having been carried out on a sample site or surface. The sample site or surface may be that of a machine, a piece of equipment or a utensil used in a manufacturing process.

More specifically, in a preferred embodiment, the sample site is the surface of a piece of equipment, a machine, a tool or any instrument or utensil used in the manufacture of health products, pharmaceuticals or medicines. Suitably, the sample site may be any work surface. The manufacturing machine or equipment is not limited to those for use in the pharmaceutical industry. In a still preferred embodiment, the sample site or surface is that of any laboratory equipment or machinery.

The method of verification or validation of a cleaning process comprises the spectroscopic evaluation of a substance or product on a sample site or surface using Chemical Imaging. Preferably, the Chemical Imaging may Infrared Chemical Imaging. Suitably, the Infrared Chemical Imaging may be Near Infrared-Chemical Imaging (NIR-CI) or Mid-Infrared Chemical Imaging (MIR-CI). The current inventors are the first to use NIR Chemical Imaging in a method of cleaning validation/verification.

The substance or product may be any type of contaminant, for example, such as an active ingredient, a residue, a product, a detergent, a microbe or any other contaminant. The sample site may be any surface. More specifically, in a preferred embodiment the sample site is the surface of a piece of equipment, a machine, a tool, or any instrument or utensil used in the manufacture of health products, pharmaceuticals or medicines or any laboratory equipment or machinery or any work surface. The surface may be comprised of stainless steel, glass, Perspex, or any other typical manufacturing equipment surface.

The method of validation or verification a cleaning process comprises:
(i) capturing an image of the surface using Infrared Chemical Imaging;
(ii) utilising at least one algorithm to interpret the captured image thereby determining the amount of substance or product present on the surface; and
(iii) determining if the amount of detected substance, if any, exceeds a threshold value.

Accordingly, in one aspect of the invention, there is provided a method of validating or verifying a process for cleaning a surface contaminated with at least one chemical substrate, comprising the steps of:
(i) capturing an infrared image of the surface using infrared chemical imaging;
(ii) utilising at least one algorithm to interpret the captured image to extract an infra-red signal from the at least one chemical substrate to determine the amount of the at least one chemical substrate present on the surface; and
(iii) determining if the amount of the at least one detected chemical substrate exceeds a threshold value, thereby indicating that a repeat cleaning process is required or thereby indicating that no further cleaning is required.

Preferably, the method of the invention, can be implemented whereby at least one of the steps (ii) or (iii) are carried out in situ at the location of the surface. This is advantageous over the analysis being carried out off site or remote from the testing point, as it enables, repeat or verification testing to be carried our immediately. Such method can be carried out by a suitable portable or handheld device.

Suitably, in the method of the invention, the amount of detected chemical substrate may be determined or quantified by comparing with a known standard. For example, the pixel saturation for an image of a detected chemical substrate may be compared to a standard consisting of the pixel saturation of a known concentration of chemical substrate. In one embodiment, the threshold value may be less that the LOQ but greater than the LOD of the at least one chemical substance.

In a preferred embodiment, at least one algorithm is applied to the captured data to counteract or extrapolate signal from background noise, that is, to compensate for any low signal to noise effects. Such effects are common in situations where low concentrations of chemicals on surfaces such as steel need to be quantified. For example, the surface may be textured or may have curvature, and in such cases, there can be serious problems arising from reflection. Preferably, the algorithm of step (ii) is capable of performing a signal to noise enhancement step.

The cleaning process is approved or denied depending on whether substance or product concentration meets pre-determined specifications or criteria. The cleaning process will be approved or validated if the amount of detected substance does not exceed a threshold value. The cleaning process will not be approved or validated if the amount of detected substance exceeds a threshold value. The threshold value is the level or amount of substance that can remain on the surface without adversely affecting or contaminating the surface or any process that may be subsequently carried out on that surface or any product produced on the surface.

The Infrared Chemical Imaging may be Near-Infrared Chemical Imaging (NIR-CI) or Mid-Infrared Chemical Imaging (MIR-CI).

The Infrared-Chemical Imaging is used to visualize the spatial distribution of the chemical compounds/substance/product in/or a sample, providing an image, that is a chemical image of the spatial distribution. The Chemical Image may be constructed using pushbroom acquisition or by staring imager configuration. In a preferred embodiment, staring imager configuration is used to construct the chemical image. Each sample measurement generates a hyperspectral data cube containing thousands of spectra. As mentioned above, in a preferred embodiment of the invention a first algorithm, as shown in FIG. 13, is used for pre-processing of hyperspectral data cube. The algorithm excludes the background surface from the calculation. The ability for interaction between hyperspectral cube and algorithm to accurately extract the background at such low concentrations as are required for cleaning validation studies, overcomes sensitivity problems associated with CI-NIR detection on surfaces, for example glass, Perspex, ceramics or steel. These surfaces have a tendency to be texturised or possess curvature and so signal interference in the chemical imaging step is common. Thus, a special algorithm must be applied to the data to compensate for any distortion in signal or adverse effects of low or poor signal to noise.

In a further preferred embodiment of the invention a second algorithm, as shown in FIG. 14, is used for PLS-DA (Partial least squares discriminant analysis). The second algorithm calculates the amount of chemical compounds/substance/product present on the surface based on spectral data per pixal.

The method of the current invention is superior to prior art methods utilising single point NIR (for example that as described by U.S. Pat. No. 7,557,923). In addition, the method as described by the current inventors uses a constant light source, which is advantageous over the light pulses utilised by the prior art method outlined by the authors of U.S. Pat. No. 7,557,923, as it allows for great consistency of sample analysis. In addition, U.S. Pat. No. 7,557,923 utilise a wide band light detector while the method as developed by the current inventors uses NIR/MIR cameras.

A second aspect of the invention provides a method of assessing homogeneity of blended materials or a tablet or the detection of counterfeit pharmaceutical tablets comprising the use of Near-infrared Chemical Imaging (NIR-CI) or Mid-Infrared Chemical Imaging (MIR-CI). The method comprises:
 (i) capturing an image of the material or tablet using Infrared Chemical Imaging; and
 (ii) utilising at least one algorithm to interpret the captured image thereby assessing homogeneity of the material or a tablet.

Suitably, the Infrared Chemical Imaging may be Near-Infrared Chemical Imaging or Mid-Infrared Chemical Imaging.

This is primarily because the sample can remain stationary and the field of view would be comparable with that currently used during conventional swabbing techniques (circa 25 cm$^2$).

This method is of particular interest within the pharmaceutical industry for sample analysis and would be considered to pose the greatest potential for use as a cleaning verification device. This is primarily because the sample can remain stationary and the field of view would be comparable with that currently used during conventional swabbing techniques (circa 25 cm$^2$).

BRIEF DESCRIPTION OF THE FIGURES

FIG. 13: Algorithm for Pre-processing of hyperspectral data cube

FIG. 14: Algorithm for PLS-DA (Partial least squares discriminant analysis).

Figure 1:
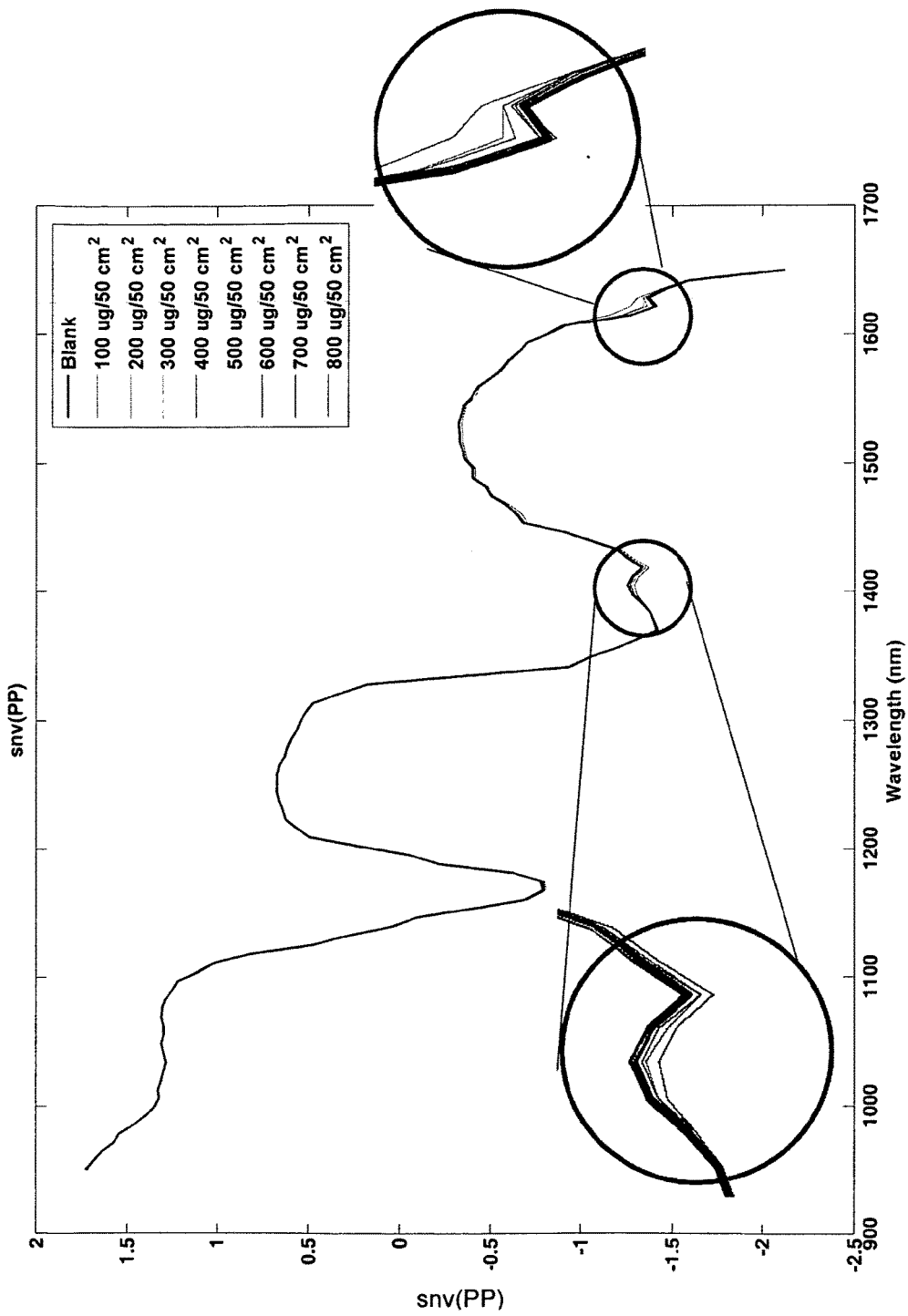
FIG. 1: Standard Normal Variate (SNV) of reflectance spectra for lactose on Perspex.

The current invention will now be described with reference to the following examples and figures. It is to be understood that the following detailed description and accompanying figures, are exemplary and explanatory only and are intended to provide a further explanation of the present invention, as claimed and not to limit the scope of the invention in any way.

DETAILED DESCRIPTION OF THE INVENTION

The current inventors have developed a method of cleaning verification comprising the use of Near-Infrared or Mid-Infrared Chemical Imaging, which can provide information on a substantial sample site or surface and rapidly quantify the contaminant levels remaining on product contact equipment following the execution of cleaning activities. The system of the invention is advantageous over the prior art as when at least one algorithm is applied to the captured data to counteract or extrapolate signal from background noise, that is to compensate for any low signal to noise effects, repeatable, accurate and precisions measures at cleaning validation concentrations on surfaces can be achieved, even with traditionally difficult surfaces such as steel, where signal to noise concentrations can be low at LOQ/LOD levels.

The method of the current invention advantageously removes some significant variables identified with VRL's and enable an analytical technique that can significantly reduce the time and cost associated with cleaning procedure development.

The method also supports the transition away from once-off cleaning validation towards continuous cleaning process verification. This would be in-line with regulatory expectations and pharmaceutical manufacturing needs. Importantly, the method can adapted for use with both hand held and in line devices capable of detecting active ingredient and detergent residue levels.

The method of the current invention is further advantageous over the existing time consuming and labour intensive method of swabbing and HPLC/alternative instrument analysis.

Utilisation of the current method will leave to an increased frequency of equipment cleaning process verification which will in turn reduce the risk of active and detergent cross-contamination and thereby enable higher acceptance criteria for active and detergent carryover. As the pharmaceutical manufacturing industry transitions towards these continuous verification philosophies the requirement for rapid analytical technologies as become essential in order to sustain robust and lean equipment cleaning processes. Advantages of the current method include the fact it is non-destructive, non-contact, it gathers multi-constituent information, and is sensitive to minor components.

EXPERIMENTAL

The inventors analysed the effectiveness of chemical imaging in the method of the invention described to distinguish between a contaminant residue and a stainless steel background surface. Lactose was chosen as the contaminant residue. Lactose is deemed representative of materials used in pharmaceutical formulations. Stainless steel, glass and Perspex surfaces were chosen as they were deemed to be typical of materials of construction for equipment used in pharmaceutical manufacture. Steel in particular is an excellent test substrate as it is know that measurements at low concentrations in the range of those required for cleaning validation studies are difficult as signal to noise ratios can be quite low, making validation of detection methods difficult to achieve.

Example 1

The first experiment carried out was with a lactose sample in a water and alcohol dilution series, which was placed on 10 cm×10 cm perspex coupon.

Materials and Methods
Solution
 0.1000 g of lactose was dissolved in 20 ml of water and mixed with 80 ml of ethanol.
Coupon Preparation
 Coupons were washed with hot water and dried
 Blank was sprayed twice with a 80% ethanol solution and left dry
 Concentrations C1 to C8 were achieve by successive cycles of spraying lactose solution over the coupon and drying, i.e. once to C1, twice to C2, three time to C3, . . . , and eight times to C8.
 Hyperspectral images were acquired.
 Data analysis
 Concentration over the coupon was estimated according with the following equation:

$$\text{Concentration}\left(\frac{\mu g}{50 \text{ cm}^2}\right) = \frac{d*b*e*50}{c*a}$$

| a | Coupon Area | 100 cm^2 |
| b | Factor | 0.5 |
| c | Density | 0.8 g/ml |
| d | Each spray mass | 0.332 g |
| e | Solution concentration | 1000 g/ml |

Cleaning validation coupons, 316 stainless steel, #4 finish, 10 cm×10 cm SS316-#4

Figure 2:
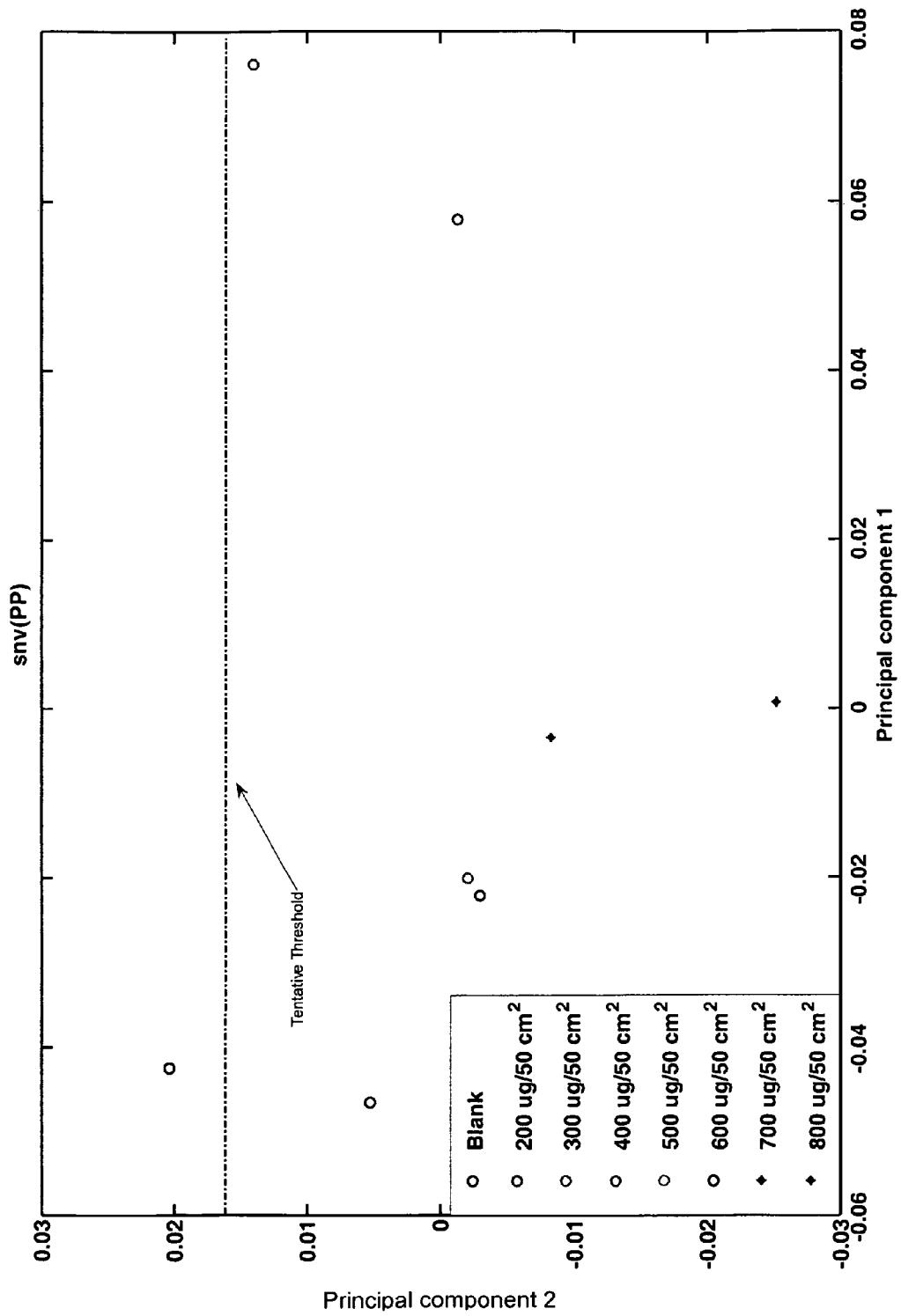
FIG. 2: Principal component score plot of Standard Normal Variate (SNV) of reflectance spectra for lactose on Perspex.

Cleaning validation coupons, Perspex (Acrylic), 10 cm×10 cm (Refer to Appendix 1 for Certificates of material authenticity).
Results
 There was an identifiable peak present at 1440 and 1620 nm as illustrated in FIG. 1. Both peaks exhibited an increase in strength as the concentration of the sample increased. This study confirms the ability of the technology to quantify lactose concentrations as low as 100 ug/100 cm$^2$ from a transparent Perspex material. FIG. 2 illustrates the principle component score plot of Standard Normal Variate (SNV) of reflectance spectra for lactose on Perspex.

Example 2

Figure 3:
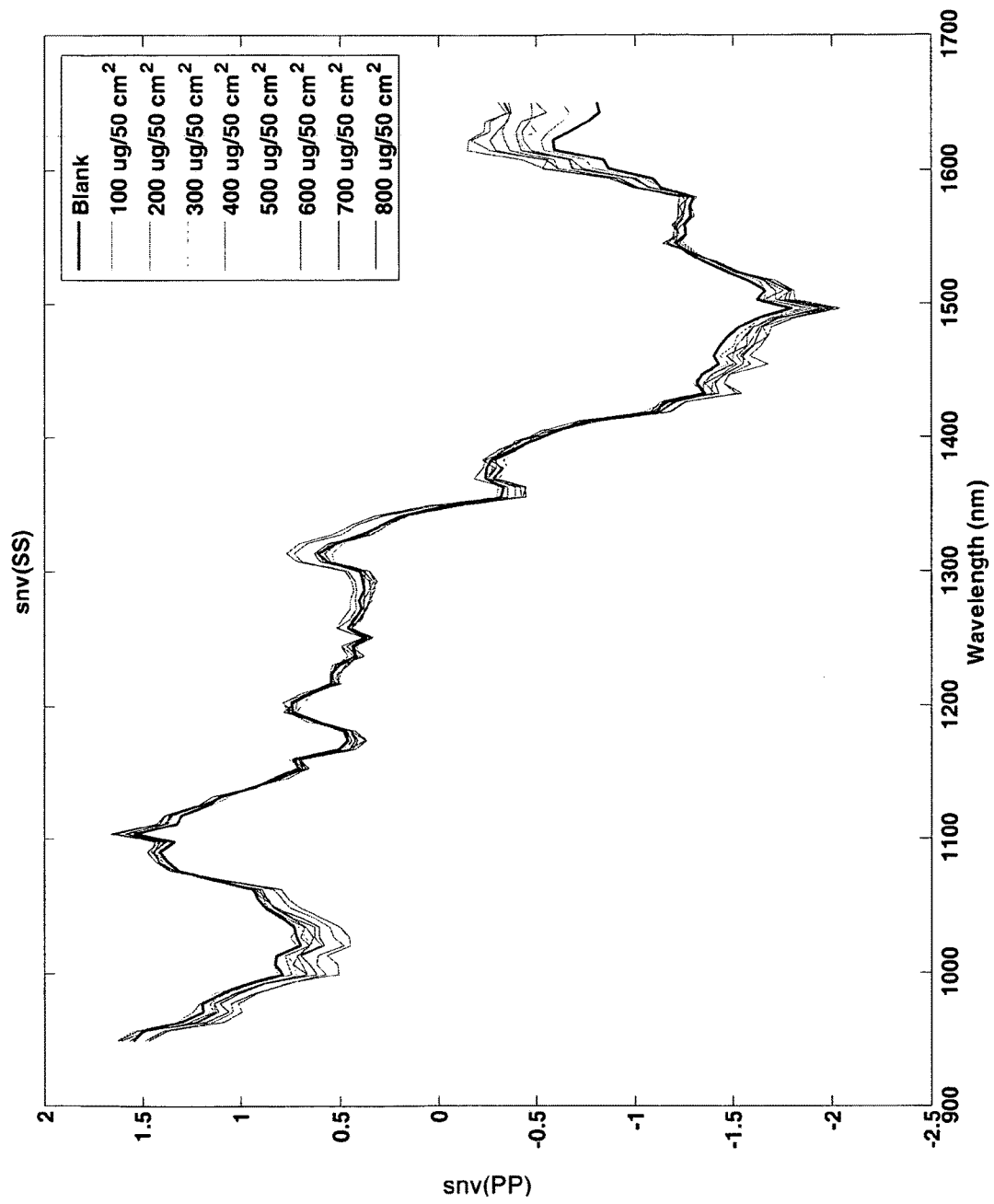
FIG. 3: Standard Normal Variate (SNV) of reflectance spectra for lactose on stainless steel.
Figure 4:
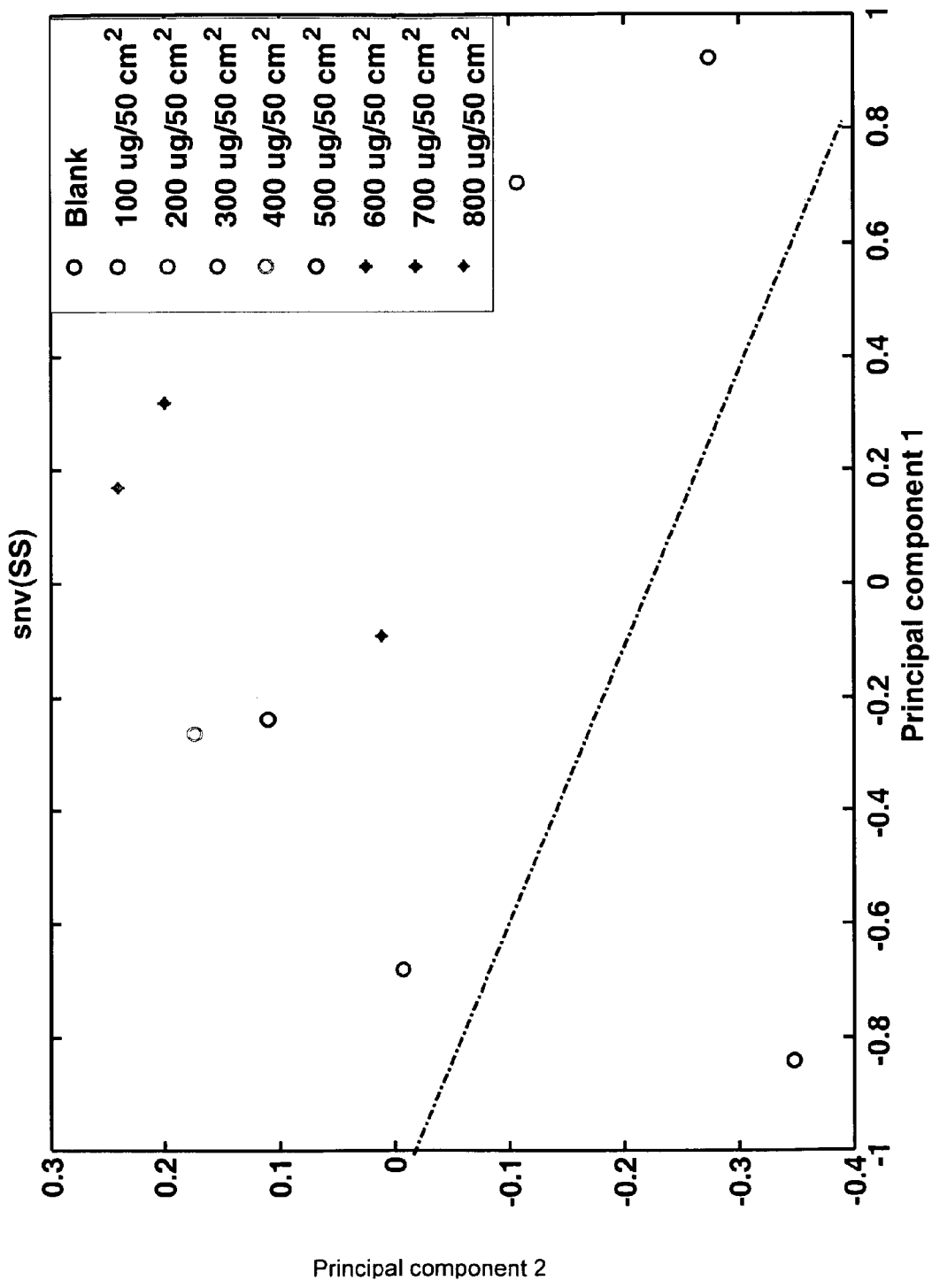
FIG. 4: Principal component score plot of Standard Normal Variate (SNV) of reflectance spectra for lactose on stainless steel.
Figure 5:
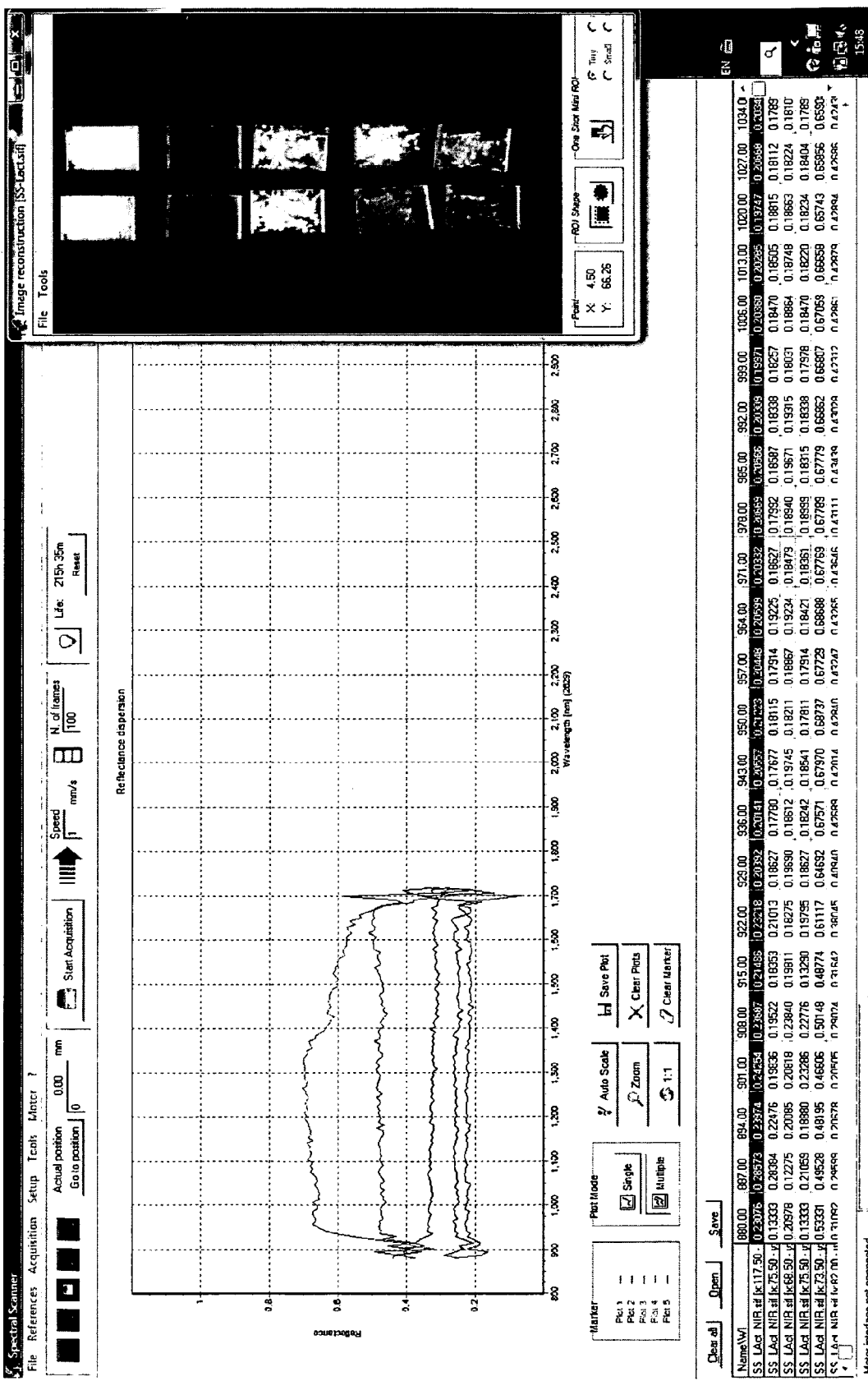
FIG. 5: Spectra of the variance of background.

The second experiment carried out was with a lactose sample in a water and alcohol dilution series, which was placed on 10 cm×10 cm stainless steel coupon.
Results
 There was an identifiable peak present at 1340 and 1620 nm as illustrated by FIG. 3. Both peaks appeared to exhibit an increase in strength as the concentration of the sample increased. There was excellent separation of spectra per concentration sample. This study confirms the ability of the technology used in the method of the invention to quantify lactose concentrations as low as 100 ug/100 cm$^2$ from Stainless Steel material. Such results are difficult to achieve using prior art methods due to low signal to noise issued on steel. FIG. 4 illustrates the principle component score plot of Standard Normal Variate (SNV) of reflectance spectra for lactose on stainless steel.
Conclusion
 In conclusion, the experimental work was successful in confirming that NIR-CI used in the method of the invention is an appropriate analytical method for identification of individual components—in this case—lactose. It has been demonstrated that the method has sensitivity capability as low as 100 ug/100 cm$^2$. It has been demonstrated that the method has capability to detect residual concentrations of lactose from both Perspex and stainless steel materials.

Example 3

Figure 6:
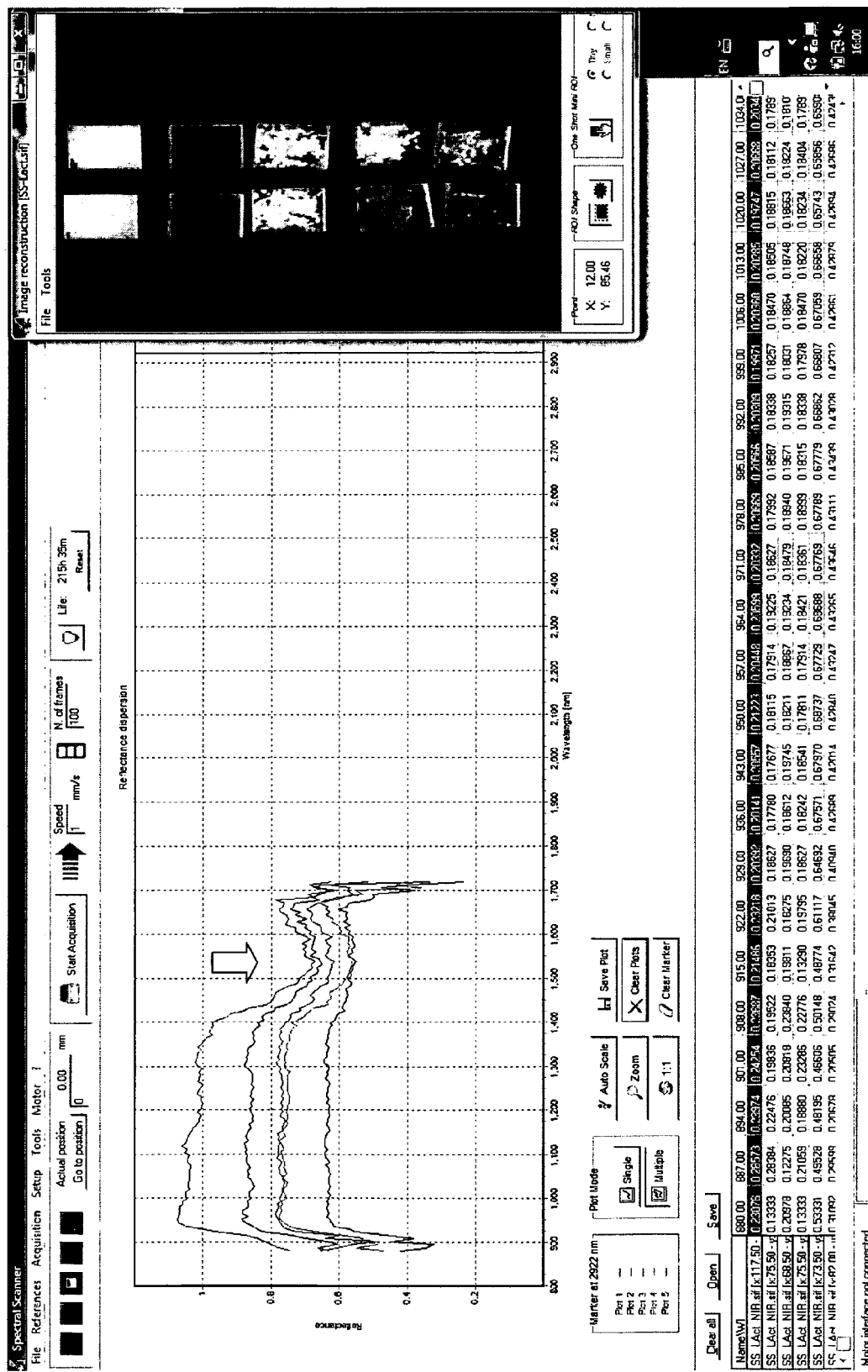
FIG. 6: lactose dip from all concentrations, 10% (green), 5% (blue), 2.5% (red), 1.25% (grey), 0.625% (black).
Figure 7:
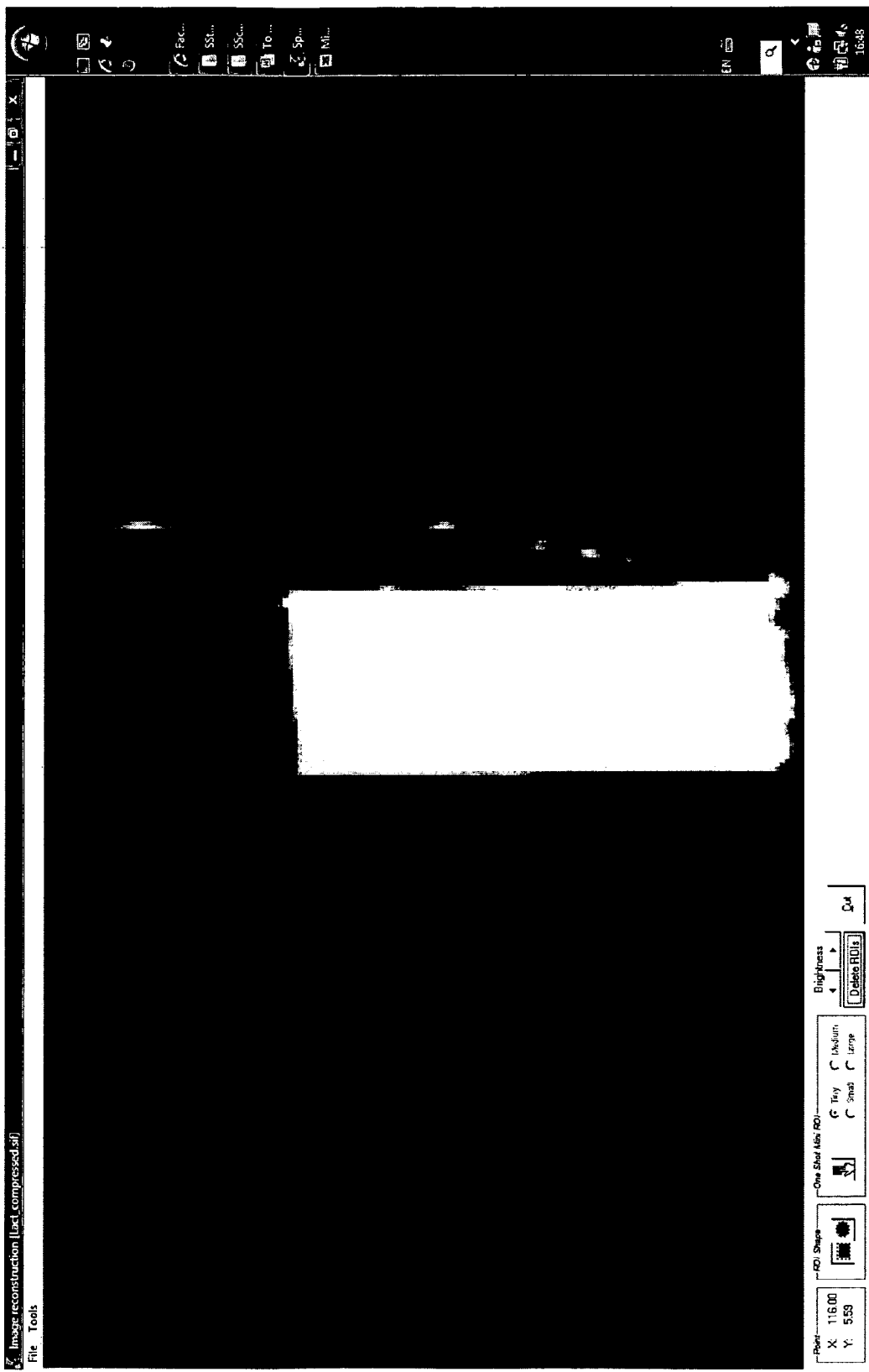
FIG. 7: Lactose powder scan.

This experiment was carried out using a lactose sample in an alcohol dilution series, which was placed on 2 cm×2 cm stainless steel tiles.
Materials and Methods
 1) Dilute series of lactose samples in alcohol.
  5 g lactose in 50 ml water or 10% dilution. Then dilute down into a 5%, 2.5% and 1.25% dilution.
 2) Pipette dilutions onto the stainless steel slides in 0.1 ml samples.
 3) Air dry slides.
 4) Remove slides and scan to get the spectra for the lactose.
 5) Obtain hyperspectral images using a pushbroom line-scanning HSI instrument (DV Optics Ltd., Padua, Italy), operating in the NIR (950-1700 nm) wavelength range.
Results
 A variance was identified in the spectra of samples, which should have given uniform spectra (FIG. 7). There was also a variance in the background spectra, as illustrated by FIG. 6. These variances were down to the fact that the stainless steel tiles were all separate and the cut edges of the stainless steel were giving off slight reflectance, which were therefore giving slightly different spectra. The way to fix this problem was to find a large piece of stainless steel, which would give one uniform background. However, after this scan it was seen that there was a characteristic dip in the spectra of the lactose at about 1400-1660 nm. This dip was evident in the spectra from the first scan and also in the spectra from each dilution in the series. This was considered to be an indicator peak for lactose and confirms applicability of this analytical method for detection of low residue concentrations.

Figure 8:
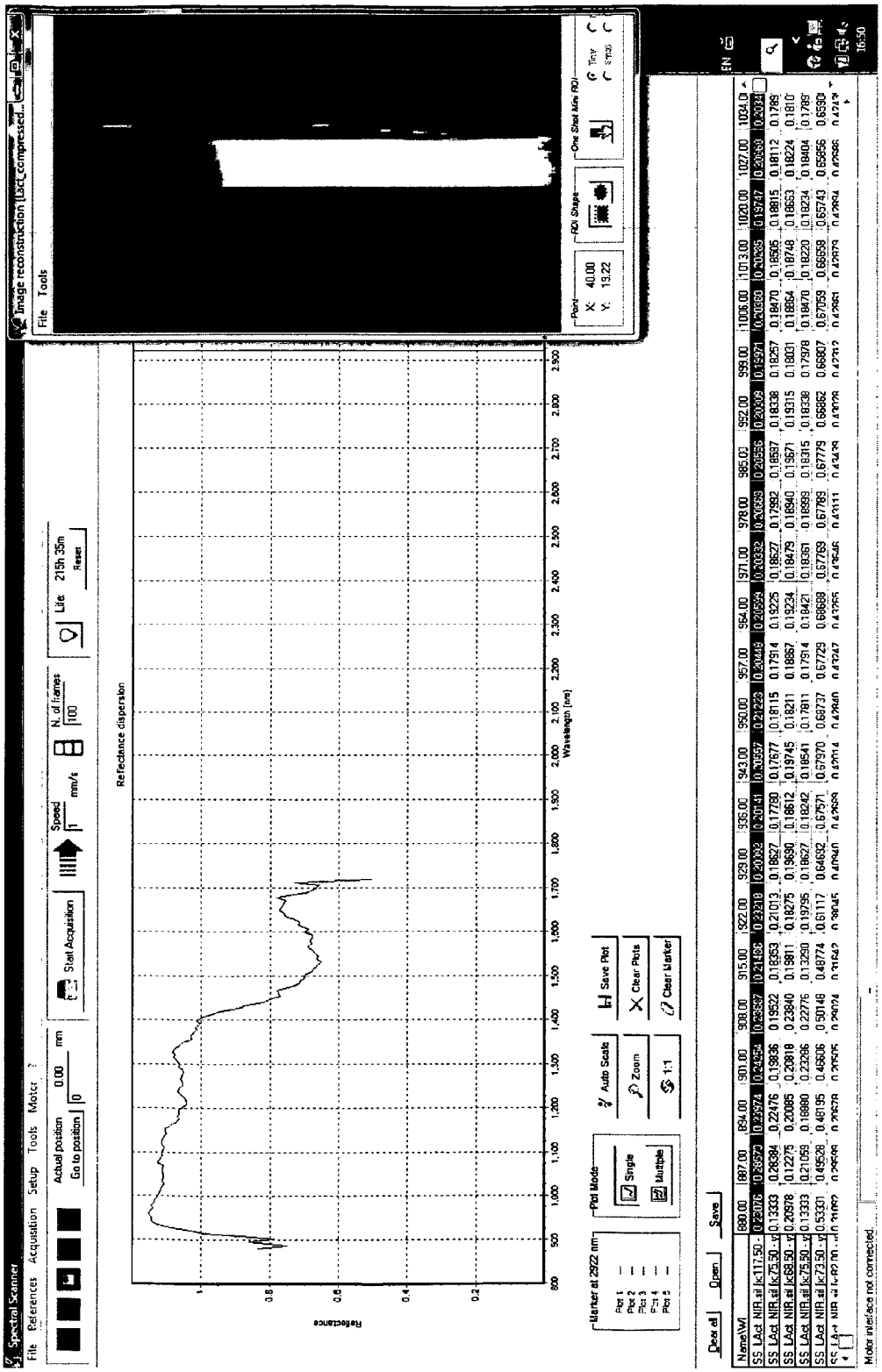
FIG. 8: Spectra of lactose powder.

The inventors clarified that the characteristic seen in the previous scans was a characteristic of the lactose and not a characteristic of the stainless steel background. FIG. 8 illustrates a scan of a sample of pure lactose powder. The spectra again showed the characteristic of the lactose sample, which had been seen from the previous scans. This meant that the dip at 1400-1660 nm was the characteristic looked for in each scan.

Example 4

This experiment was carried out using a nitrate sample in an alcohol dilution series which was placed on 2 cm×2 cm stainless steel tiles.
Materials and Methods
 1) Dilute series of nitrate samples in alcohol.
  5 g nitrate in 50 ml water or 10% dilution. Then dilute down into a 5%, 2.5% and 1.25% dilution.
 2) Pipette dilutions onto the stainless steel slides in 0.1 ml samples.
 3) Air dry slides.
 4) Remove slides and scan to get the spectra for the lactose.
 5) Obtain hyperspectral images using a pushbroom line-scanning HSI instrument (DV Optics Ltd., Padua, Italy), operating in the NIR (950-1700 nm) wavelength range.

Results and Findings

Figure 9:
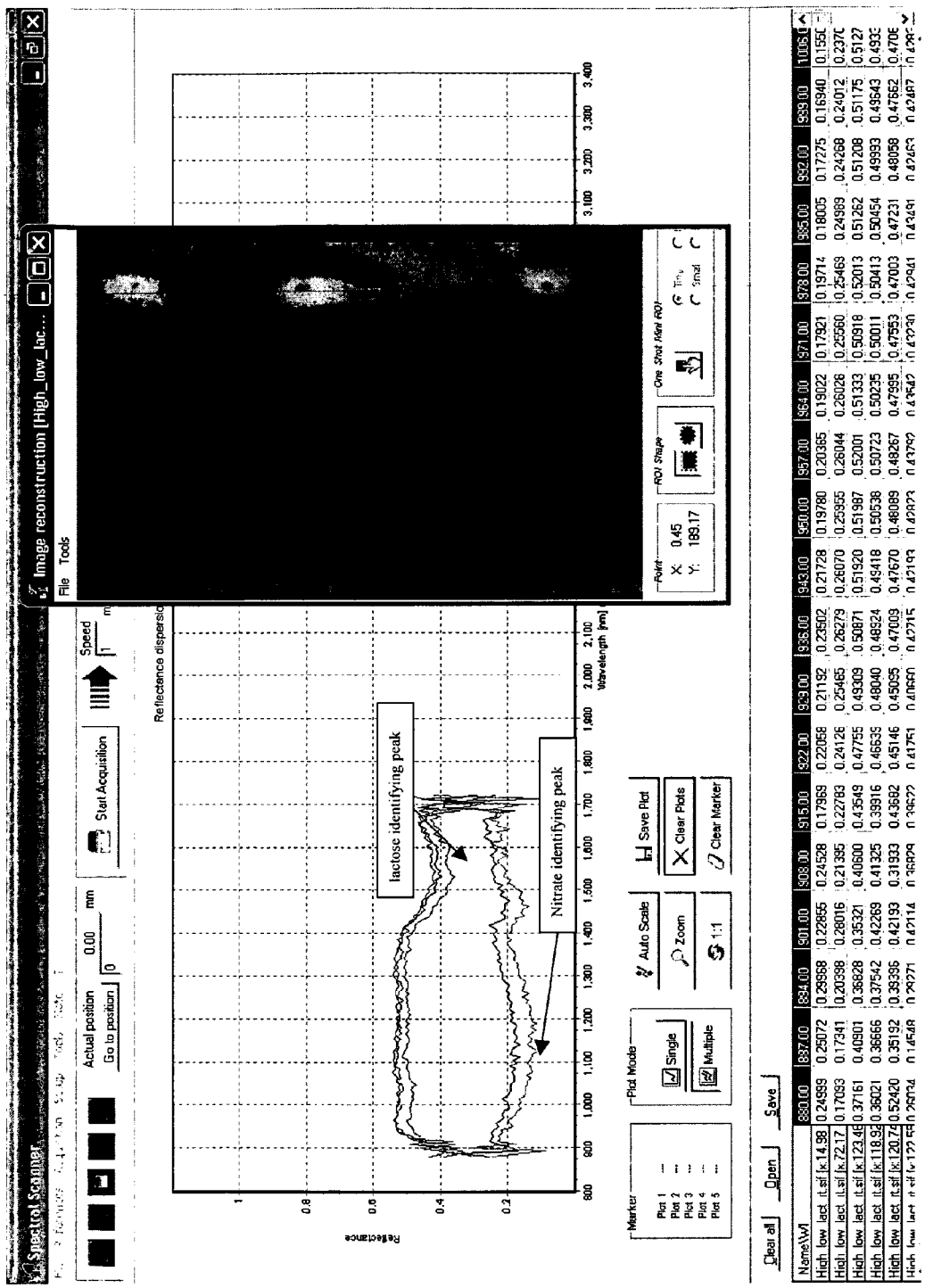
FIG. 9: Nitrate and lactose dips from a variety of concentrations.

A characteristic dip in the nitrate spectra at about 1000-1100 nm, FIG. 9. This dip was evident in the spectra from the first scan and also in the spectra from each dilution in the series. This was considered to be an indicator peak for the component and confirms applicability of this analytical method for detection of low residue concentrations.

Mean Trend Analysis

Figure 10:
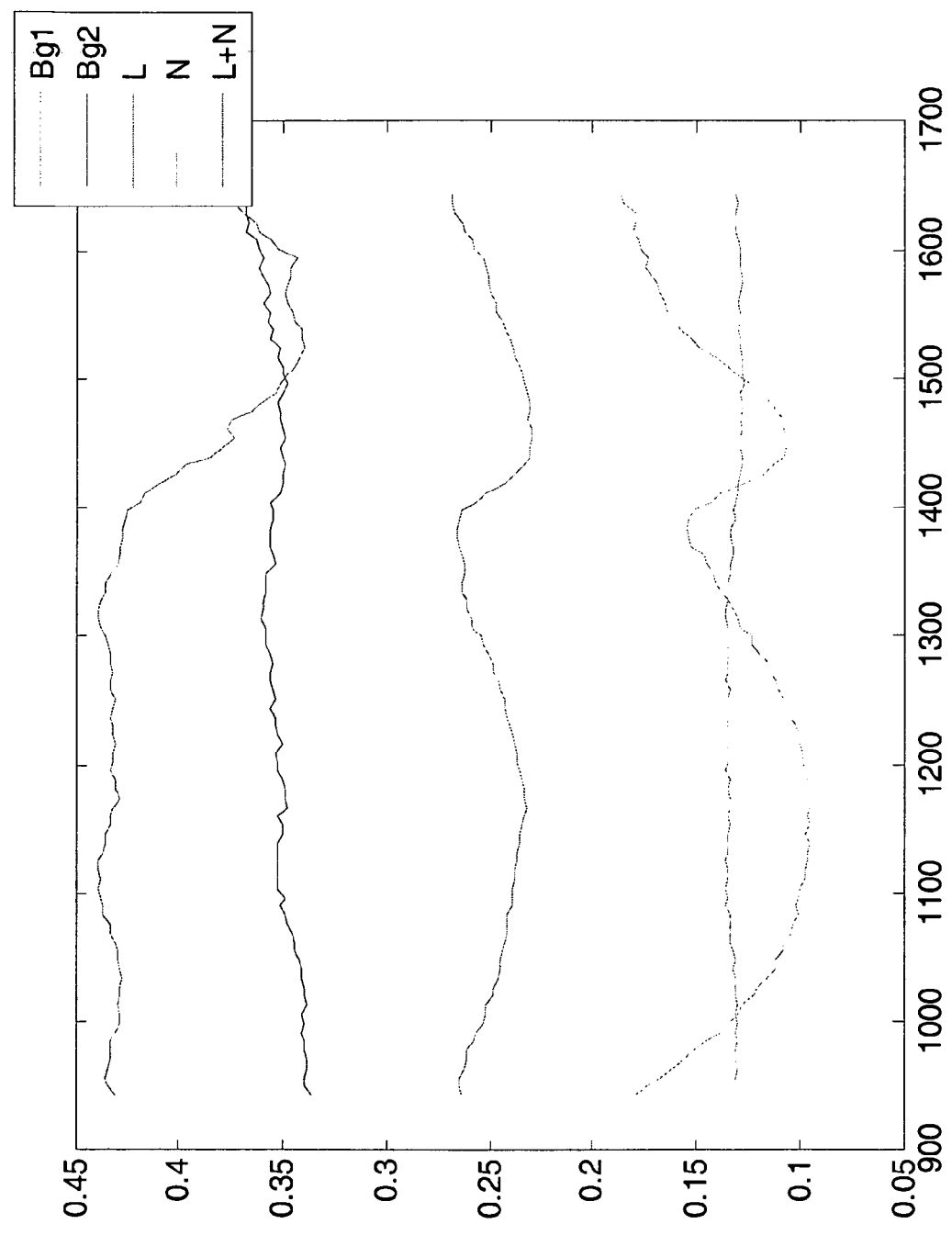
FIG. 10: Nitrate, lactose and background (stainless steel) mean trend data.

The mean spectra for lactose, nitrate and background (stainless steel) were graphed in FIG. 10. It was confirmed that there are distinctive trend lines for both lactose and nitrate residues.

Principle Component Analysis and Imaging

Figure 11:
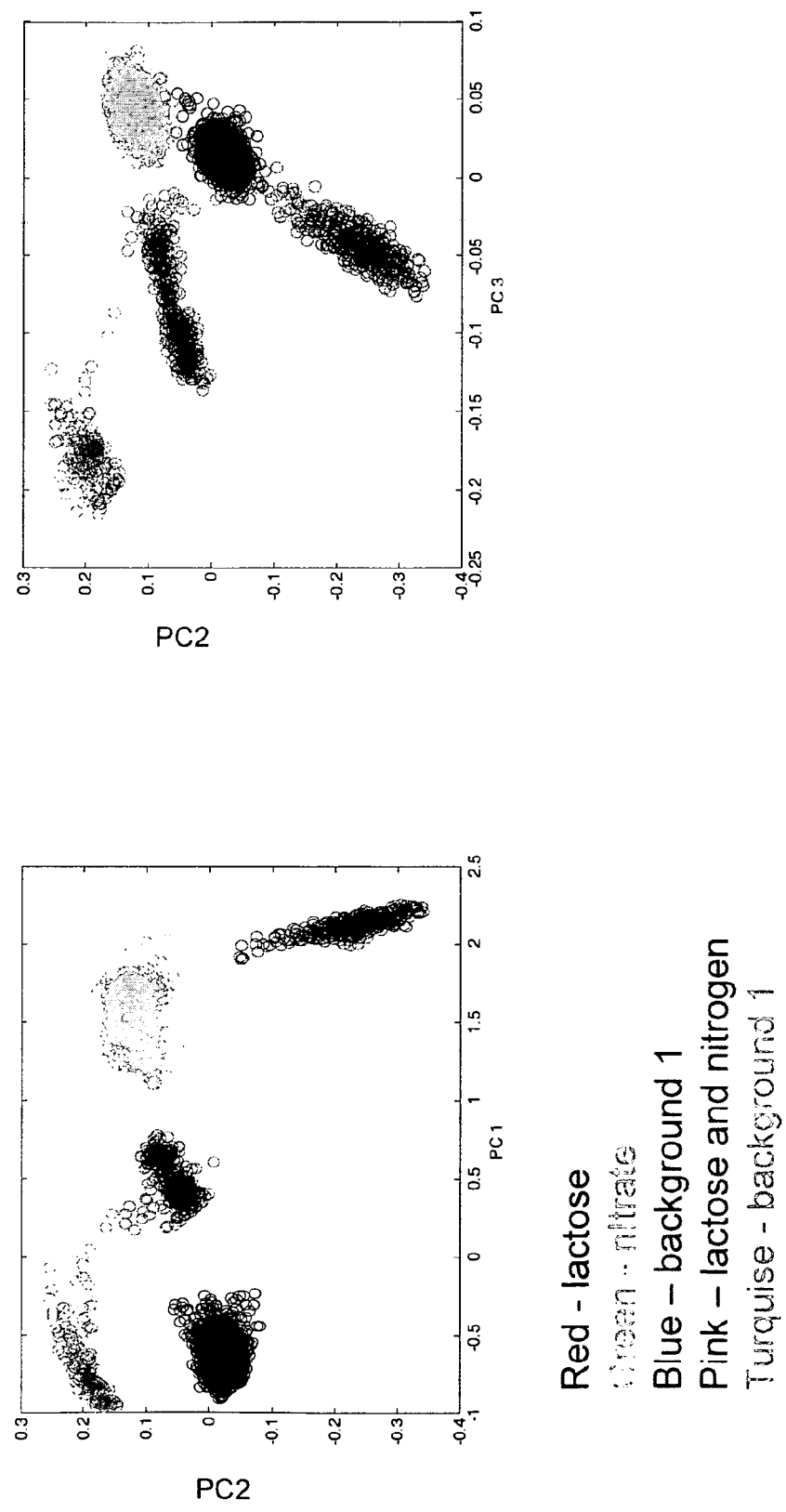
FIG. 11: Principle component analysis.
Figure 12:
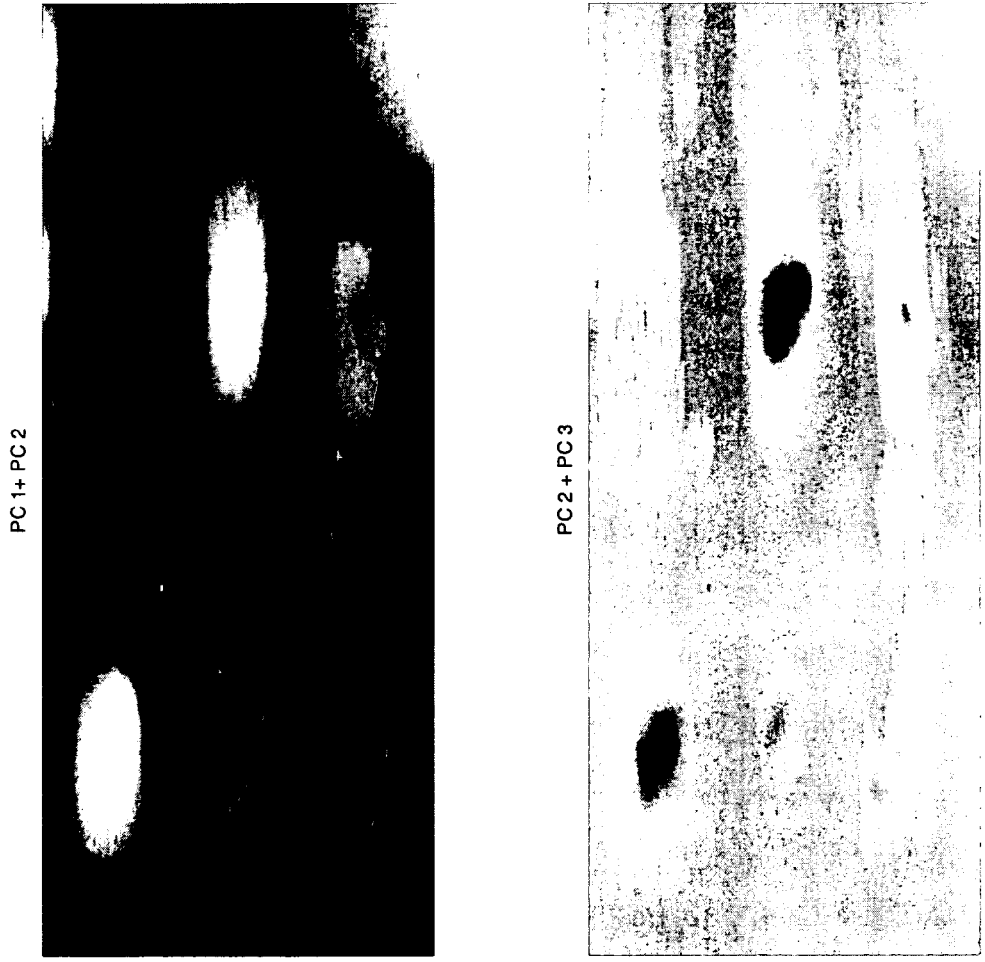
FIG. 12: Principle component image.

The principle components (lactose, nitrate and background) were analysed using principle component analytical techniques and illustrated in FIGS. 11 and 12.

The principle component analysis and imaging was successful in isolating the individual spectra for lactose, nitrate and background stainless steel.

Conclusion

In conclusion, the experimental work was successful in confirming that NIR-CI used in the method of the invention is an appropriate analytical method for identification of individual components—in this case—lactose and nitrate. It has demonstrated that this method has application within the pharmaceutical industry as a method of equipment cleaning validation.

Example 5

Figure 15:
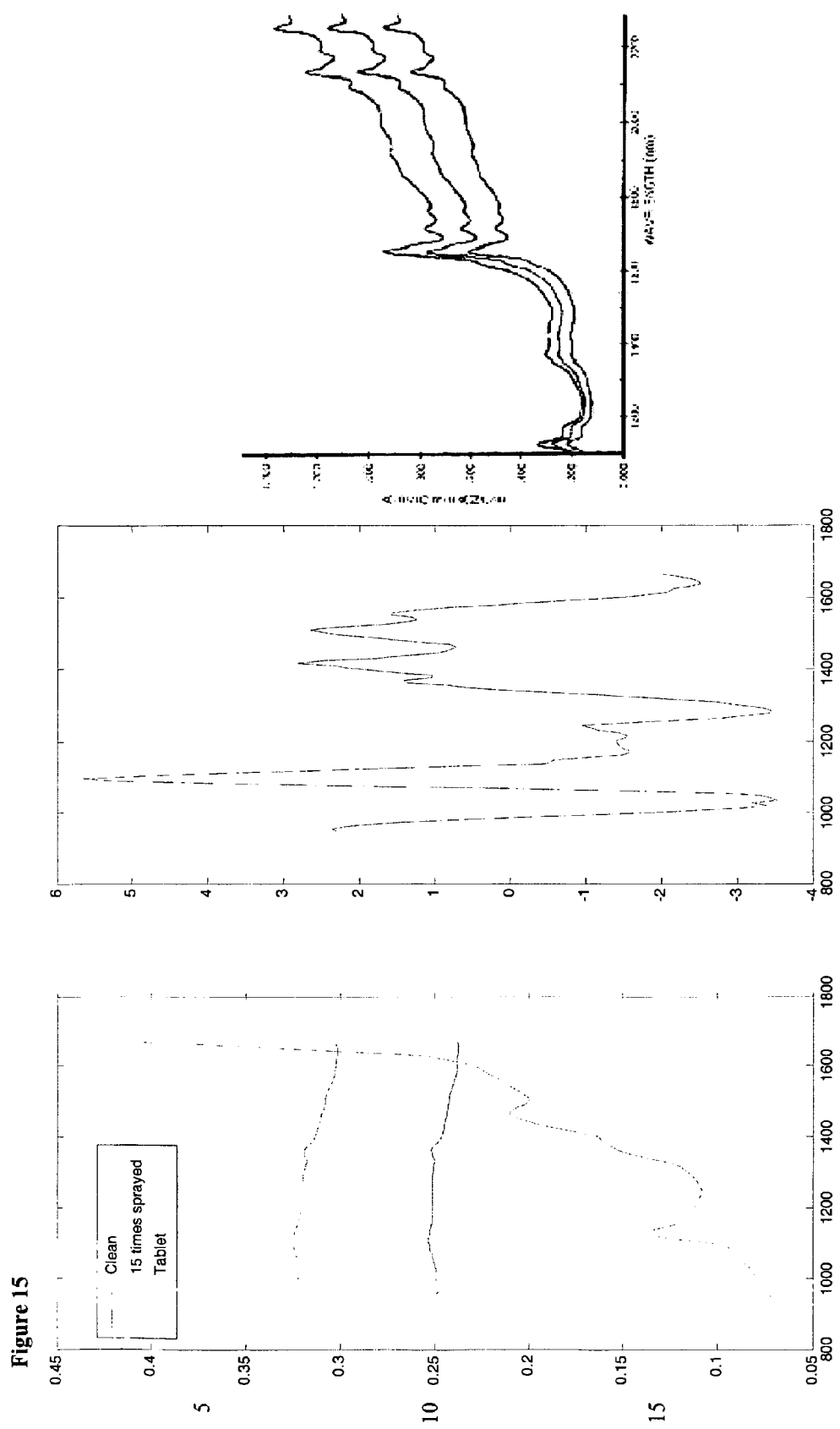
FIG. 15: Spectra Pharmaceutical Ingredients.
Figure 16:
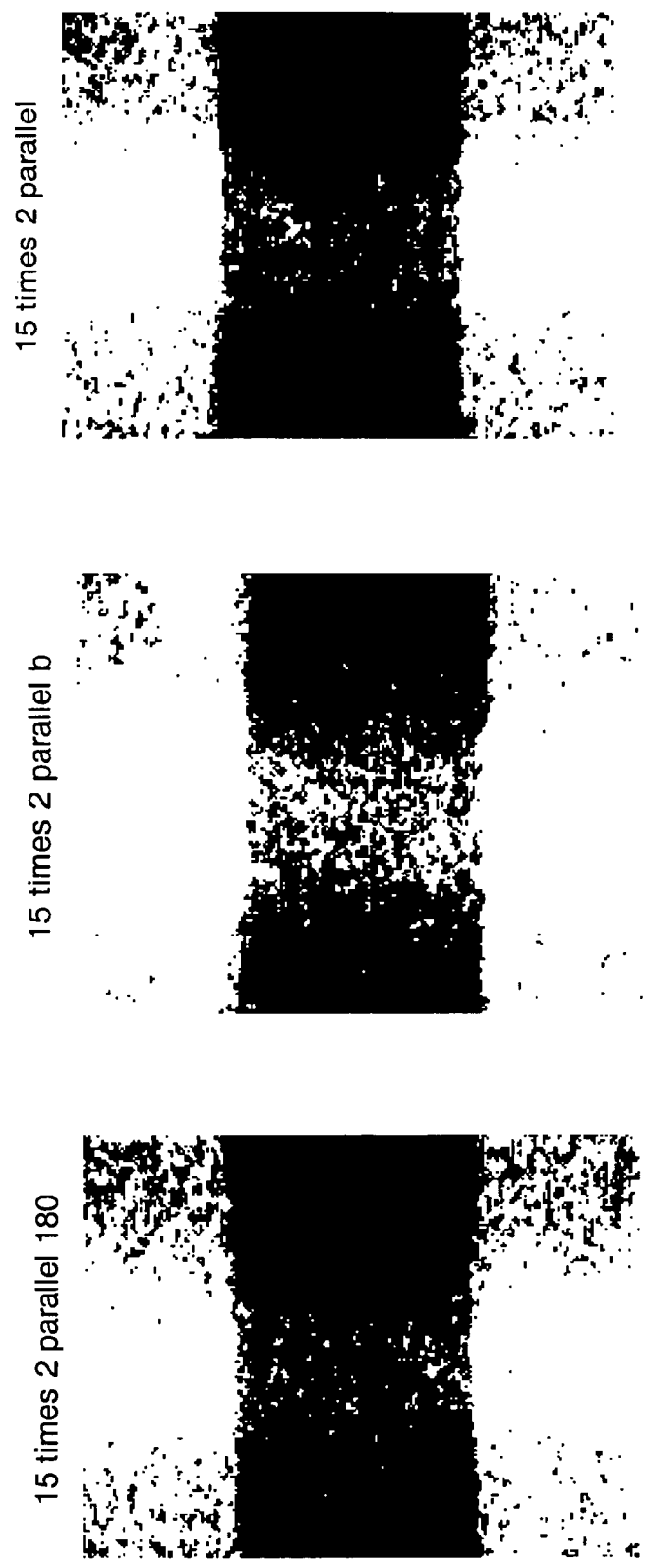
FIG. 16: Spectra for Acetyl Salicylic Acid

This experiment was carried out using chemical entities, caffeine, acetyl salicyclic acid and blends placed on stainless steel. The results are illustrated in FIGS. 15 and 16, which illustrate spectra for acetyl salicylic acid.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

REFERENCES

1. FDA Draft Guidance 'Process Validation General Principles and Practices' Current Good Manufacturing Practices. November 2008.
2. PwC paper Pharma 2020: The Vision Price Waterhouse Coopers, 2009
3. D. W. Mendenhall, "Cleaning Validation," *Drug Development and Industrial Pharmacy* 15 (13), 2105-2114 (1989)
4. D. A. Le Blanc, "'Visually Clean' as a Sole Acceptance Criteria for Cleaning Validation Protocols," *PDA J. Pharm Sci. And Technology.* 56 (1), 31-36 (2002).
5. Richard J. Forsyth et al, "Risk-Management Assessment of Visible-Residue Limits in Cleaning Validation" *Pharm. Technol.* 30, 104-114 September (2006)
6. Richard J. Forsyth, "Ruggedness of Visible Residue Limits for Cleaning Validation" *Pharm. Technol* 33, 102-111 March (2009)
7. Elizabeth Galella et al., "Cleaning Verification: Method Development and Validation using Ion Mobility Spectrometry" *Pharm. Technol.* 33, 60-63 July (2009)
8. Kevin J. Kolodsick et al., "Enhancing Drug Development by Applying LC-MS-MS for Cleaning Validation in Manufacturing Equipment" *Pharm. Technol.* 30, 56-71 February (2006)
9. Hamilton et al., "Grazing-angle fiber-optic IR reflection-absorption spectrometry (IRRAS) for in situ cleaning validation" Org. Process Res. & Devel., 9(3), 337-343, (2005)
10. Ravn, C. Skibsted, E. Bro, R. Near-infrared chemical Imaging (NIR-CI) on pharmaceutical solid dosage forms—Comparing Common calibration approaches. Journal of Pharmaceutical and Biomedical Analysis 48 (2008) 554-561
11. Gowen. A, O'Donnell. C. P, Cullen. P. J, Bell. S. E. J, Recent applications of Chemical Imaging to pharmaceutical process monitoring and quality control. European Journal of Pharmaceutics and Biopharmaceutics 69 (2008) 10-22

The invention claimed is:

1. A method of validating or verifying a process for cleaning a surface contaminated with at least one chemical substrate, comprising the steps of:
   (i) capturing an infrared image of the surface using infrared chemical imaging;
   (ii) utilizing at least one algorithm to interpret the captured image to extract an infra red signal from the at least one chemical substrate to determine the amount of the at least one chemical substrate present on the surface; and
   (iii) determining if the amount of the at least one detected chemical substrate exceeds a threshold value, thereby indicating that a repeat cleaning process is required or thereby indicating that no further cleaning is required, wherein the pixel saturation for the detected chemical substrate is compared to a standard consisting of the pixel saturation of a known concentration of chemical substrate.

2. The method of claim 1, wherein at least one of the steps (ii) or (iii) is carried out in situ at the location of the surface.

3. The method of claim 1, wherein the algorithm of step (ii) performs a signal to noise enhancement step.

4. The method of claim 1 wherein the threshold value is less that the LOQ but greater than the LOD of the at least one chemical substance.

5. A method of validating or verifying a cleaning process of a surface comprising:
   (i) capturing an image of the surface using infrared Chemical Imaging,
   (ii) utilizing at least one algorithm to interpret the captured image thereby determining the amount of substance present on the surface,
   (iii) determining if the amount of detected substance, if any, exceeds a threshold value, thereby indicating that a repeat cleaning process is required or thereby indicating that no further cleaning is required, wherein pixel saturation for the detected substance is compared to a standard consisting of the pixel saturation of a known concentration of substance.

6. The method of claim 5, wherein the Infrared Chemical Imaging is Near-Infrared Chemical Imaging or Mid-Infrared Chemical Imaging.

7. The method of claim 5, wherein the image is captured by staring imager configuration.

8. The method of claim 5, wherein the image is captured by push broom acquisition.

9. The method of claim 5, wherein the surface is the surface of any machine or equipment used in manufacturing, any work surface, the surface of any machine, instrument, a tool or utensil used in the manufacture of pharmaceuticals or medicine, or the surface of any laboratory equipment or machinery.

10. The method of claim 9, wherein the surface is stainless steel, glass, Perspex or any other typical manufacturing or laboratory equipment surface.

11. The method claim 5, wherein the substance is any contaminant, an active ingredient, a residue, a detergent, a product, a microbe or any other contaminant.

12. A method of validating or verifying a cleaning process of a surface comprising:
   (i) capturing an image of the surface using Infrared Chemical imaging,
   (ii) utilizing at least one algorithm to interpret the captured image thereby determining the amount of substance present on the surface,
   (iii) determining if the amount of detected substance, if any, exceeds a threshold value, wherein the captured image comprises a hyperspectral data cube and wherein a first algorithm is used for pre-processing the hyperspectral data cube and a second algorithm is used for partial least squares discriminant analysis.

13. The method of claim 12, wherein the first algorithm excludes a background from the captured image.

14. The method of claim 12, wherein the second algorithm calculates an amount of chemical substance present on said surface based on spectral data per pixel.

* * * * *